(12) United States Patent
Kamiyama et al.

(10) Patent No.: US 6,436,049 B1
(45) Date of Patent: Aug. 20, 2002

(54) THREE-DIMENSIONAL ULTRASOUND DIAGNOSIS BASED ON CONTRAST ECHO TECHNIQUE

(75) Inventors: Naohisa Kamiyama; Yoichi Ogasawara, both of Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 22 days.

(21) Appl. No.: 09/583,572

(22) Filed: May 31, 2000

(30) Foreign Application Priority Data

May 31, 1999 (JP) .......................................... 11-153082

(51) Int. Cl.[7] .............................................. A61B 8/14
(52) U.S. Cl. ..................................... 600/458; 128/916
(58) Field of Search ............................... 600/437, 407, 600/443, 504, 458, 454, 505, 526; 424/9.5, 9.51, 9.52; 382/132, 128

(56) References Cited

U.S. PATENT DOCUMENTS

| | | | |
|---|---|---|---|
| 5,469,849 A | * 11/1995 | Sasaki et al. | 600/443 |
| 5,685,310 A | * 11/1997 | Porter | 600/458 |
| 5,732,707 A | * 3/1998 | Widder et al. | 600/454 |
| 5,797,396 A | * 8/1998 | Geiser et al. | 600/407 |
| 5,833,613 A | 11/1998 | Michalakis Averkiou et al. | |
| 5,860,931 A | * 1/1999 | Chandler | 600/458 |

* cited by examiner

Primary Examiner—Marvin M. Lateef
Assistant Examiner—Ali M. Imam
(74) Attorney, Agent, or Firm—Oblon, Spivak, McClelland, Maier & Neustadt, P.C.

(57) ABSTRACT

In ultrasound diagnosis, a contrast echo technique on three-dimensional scanning is used with a contrast agent injected into an object. Before injecting the contrast agent and under the injection thereof, a blood vessel is continuously and securely targeted and depicted in displayed images. To realize this, a diagnostic ultrasound apparatus has means for acquiring an echo signal by scanning a three-dimensional region of an object with an ultrasound beam, means for producing three-dimensional image data based on the echo signal, means for displaying the three-dimensional image data, means for specifying, for example, from the echo signal, a timing at which injecting an ultrasound contrast agent into a region to be scanned of the object is started, and means for switching over at the specified timing display states of the three-dimensional image data to be displayed by the displaying means. By way of example, the switchovers are carried out such that data produced by projecting the three-dimensional image data on a minimum intensity projection technique are displayed before injecting the contrast agent, while data produced by projecting them on a maximum intensity projection technique are displayed after the start of injecting the contrast agent.

34 Claims, 8 Drawing Sheets

(BEFORE INJECTION OF CONTRAST AGENT)

(AFTER INJECTION OF CONTRAST AGENT)

THREE-DIMENSIONAL ULTRASOUND DIAGNOSIS BASED ON CONTRAST ECHO TECHNIQUE

BACKGROUND OF THE INVENTION

1. Field of the Invention

The present invention relates to a diagnostic ultrasound apparatus capable of providing a three-dimensional image by scanning in real time a three-dimensional region of an object to be diagnosed and a method of switching over the images, and in particular, the apparatus and the method directed to a contrast echo technique with a contrast agent of which essential constituent is microbubbles, in which the contrast echo technique is suitable for observation of dynamics of flows of blood through vessels, observation of dynamics of flows of blood in an organic tissue by means of detecting perfusion, and quantitative measurement of those dynamics.

2. Description of the Prior Art

Ultrasound signals have now been clinically used in various fields, in which one usage is an application to a diagnostic ultrasound apparatus. The diagnostic ultrasound apparatus acquires image signals through transmission and reception of an ultrasound signal toward and from an object and is used in a variety of modes utilizing non-invasiveness of the signal. One typical type of diagnostic ultrasound apparatus produces tomographic images of a soft tissue of a living body by using a method of ultrasound pulse reflection imaging. This imaging method non-invasively produces tomographic images of the tissue. Compared with other medical modalities such as a diagnostic X-ray apparatus, X-ray CT scanner, MRI system, and diagnostic nuclear medicine system, this imaging method is advantageous in many aspects such that real-time display is possible, a compact apparatus is manufactured at relatively lower costs, the exposure of X-rays will not occur, and blood imaging is possible thanks to ultrasound Doppler imaging.

Thus, this imaging is widely used in diagnosis of the heart, abdomen, mammary gland, urinary organs, and obstetrics and gynecology, and possesses various advantages. In particular, pulsation of the heart or motion of a fetus can be observed in real time just through a manipulation that is as simple as placing an ultrasound probe on the patient's surface. Still, since there is no need to worry about patient's exposure, screening can be carried out repeatedly many times. Furthermore, there is an advantage that an apparatus can be moved to a bedside position to examine a patient easily.

In the field of this diagnostic ultrasound apparatus, for screening the heart or abdominal organs, contrast echo imaging has newly been introduced and spotlighted recently, by which an ultrasound contrast agent (hereinafter called contrast agent) is trans-venous injected into a patient for evaluating the kinetics of blood flow. Since the trans-venous injection of a contrast agent is less invasive than trans-arterial injection type of contrast echo imaging, diagnosis using such trans-venous injection technique tends to become popular. A main constituent of the contrast agent is composed of minute bubbles (microbubbles) that act as sources of reflecting ultrasound waves. The larger the amount and concentration of an injected contrast agent is, the larger the effect of contrast imaging is. However, due to some characteristic of microbubbles of a contrast agent, a situation where radiation of ultrasounds results in a shortened duration of the contrast effect. Considering such a situation, a contrast agent having characteristics of long persistency and high durability against sound pressure has been developed in recent years.

Concurrently with such development of imaging techniques, a need for three-dimensional imaging for ultrasound diagnosis has been needed, like in the fields of the CT and MRI. In a three-dimensional volume image, information about an object in its back and forth direction is acquired in addition to information obtained from a two-dimensional tomographic image, it is possible to know more clearly shapes of tissues and dynamics of flows of blood. Thus, in conducting ultrasound diagnosis, visualizing three-dimensional images has drawn attention as a way of developing a new diagnostic field.

As one way of three-dimensional scanning, there is a technique of acquiring three-dimensional echo data as a probe of which ultrasound transducers arranged one-dimensionally is moved along the body surface of a patient. Practically, a convex probe or linearly arrayed probe for abdominal imaging is moved by hand or mechanically. Alternatively, a trans-esophagus multi-plane probe having a mechanism of rotating a sector probe is used.

However, the above one-dimensional probe requires that it take a large amount of time to acquire three-dimensional echo information itself even when any scanning method is adopted, compared to the conventional cross sectional scanning method. A fast-moving object, such as the heart, is therefore difficult to be traced with high accuracy. Even if an object does not move so fast as does the heart, distortion of images becomes too large unless a probe is located in a sufficiently secured manner.

In recent years, a diagnostic ultrasound apparatus has been researched eagerly, which comprises a probe having phased array transducers arranged two-dimensionally so as to scan an ultrasound beam three-dimensionally is used to scan a three-dimensional volume region at a frame rate closer to realtime scanning, for example, 30 frames/sec.

Though well known, the advantages of a three-dimensional volume image include, obtaining information about an image in its the back and forward direction, which has not been given by the conventional two-dimensional tomographic image; making it possible to observe a region of interest from a point viewing along in an arbitrary direction; and others. Such a three-dimensional volume image (three-dimensional information) is displayed on a two-dimensional planar display, except display that uses particular volume image display devices. This display is realized by cutting out a two-dimensional section from a three-dimensional volume image so as to provide the section image, or producing a projection image viewing a three-dimensional volume image from a specified point of view so as to provide the projection image. This way to produce projection images include a maximum intensity (luminance) projection technique (Max IP technique) and a minimum intensity (luminance) projection technique (Min IP technique).

Although the techniques of visualizing the foregoing projection images are relatively easily available for displaying an object in the air, there are some cases where they cannot offer an effective display for ultrasound images.

In other words, owing to the fact that an ultrasound image into which a contrast agent has not been injected represents an object's tissue region corresponding to the foregoing air and producing an echo signal of which intensity is relatively high, displaying a two-dimensional projected image using, for example, the maximum intensity projection technique may result in that constituents, such as tumors in tissue and blood vessels, are hidden by a tissue image portion. In this case, the minimum intensity projection technique can be used to extract blood vessels on the projection image, because echo signals from the blood vessel portion represent smaller intensities and their display luminance degrees are lower.

In contrast, when carrying out a contrast echo technique with a contrast agent injected, tissue and blood vessel systems are subject to a contrast effect and higher in luminance than organic tissue. As a result, for the contrast echo technique carried out after the start of an injection of the contrast agent, the maximum intensity projection technique is more advantageous.

In general, in cases the contrast echo technique is performed, it is not necessarily true that injecting a contrast agent is merely followed by scanning. It is necessary that both images acquired before and after injecting the contrast agent be traced sequentially in time. In the case that the maximum intensity projection (Max IP) technique or the minimum intensity projection (Min IP) technique are selectively employed, it is impossible to acquire blood vessel information endurable to those traces carried out sequentially in time. For example, when the maximum intensity projection technique is adopted, there frequently occurs that blood vessel regions are varied in an organic tissue on an image obtained before injecting the contrast agent. By contrast, if the minimum intensity projection technique is adopted, it cannot be realized that blood vessel regions are extracted securely on an image obtained after the start of an injection of the contrast agent.

SUMMARY OF THE INVENTION

The present invention has been made with consideration of the drawbacks of the above prior art. An object of the present invention is to provide a diagnostic ultrasound apparatus and a method for displaying ultrasound images, which are capable of visualizing the images in which a blood vessel is always securely depicted before and after the start of injecting a contrast agent in cases where contrast echo imaging on three-dimensional scanning is performed with the contrast agent injected.

In order to realize the above object, the present invention pay attention to the fact that, in most cases, the largeness relationship of intensity of echo signals emanated from both organic parenchyma and blood vessels is reversed when contrast echo imaging is performed on three-dimensional scanning, and has a primary feature of switching over projection techniques (that is, display techniques) between periods provided before and after the start of an injection of a contrast agent in projecting a three-dimensional volume data to a two-dimensional image. The present invention also has another feature of how such switchover timing is detected. Configurations to realize those features are detailed as follows.

A diagnostic ultrasound apparatus according to the present invention, as its basic constitution, comprises signal acquiring means for acquiring an echo signal by scanning a three-dimensional region of an object with an ultrasound beam; data producing means for producing three-dimensional image data based on the echo signal; displaying means for displaying the three-dimensional image data; specifying means for specifying a timing at which injecting an ultrasound contrast agent into the object is started; and display switchover means for switching over at the specified timing a display state of the three-dimensional image data displayed by the displaying means.

By way of example, the specifying means is composed of means for specifying, as the injection timing, an arbitrary timing specified by an operator.

Still by way of example, the specifying means is composed of means for automatically specifying the injection timing as the ultrasound contrast agent is injected. In this case, as one preferred embodiment, the specifying means has means for automatically specifying the injection timing responsively to a signal associated with a contrast agent injecting operation, the signal being given by a contrast agent injection apparatus. As another example, the specifying means has setting means for setting the injection timing from the echo signal itself. Specifically, the displaying means is means for displaying projection data obtained by projecting two-dimensionally the three-dimensional image data with a desired projection technique and the display switchover means is means for switching over the projection technique at the projection timing specified by the specifying means. A more specific example is that the setting means has at least either one of a first comparing means for specifying the injection timing by making a comparison in strength between the echo signal emanated from a tissue of the object and the echo signal emanated from a blood flow thereof and a second comparing means for making a comparison in strength between echo signals emanated from a blood flow of the object at sequential earlier and later timings so as to specify the injection timing.

In this constitution, for example, the first and second comparing means are composed of means for performing the comparison using a sum or average of intensity of at least part of the echo signal providing three-dimensional information. Alternatively, the first and second comparing means may be composed of means for performing the comparison using a sum or average of signal intensities of a group of signals constituting at least part of a region made up of the echo signal acquired at every spatial position in the three-dimensional region. Further, this comparison can be made using a sum or average of signal intensities during a certain interval.

On one hand, in the foregoing basic constitution, it is preferred that the display switchover means is composed of means for switching over an image display state on a first display technique used before injecting the ultrasound contrast agent to an image display state on a second display technique used after start of injecting the ultrasound contrast agent. In particular, it is preferred that the first display technique is composed of an image display technique displaying projection data obtained by projecting two-dimensionally the image data using a minimum intensity projection technique; displaying data produced by reversing in luminance gradations projection data obtained by projecting two-dimensionally the image data using a minimum intensity projection technique; or displaying projection data obtained by projecting two-dimensionally image data using a maximum intensity projection technique, the image data being produced by reversing the produced image data in luminance gradations. In contrast, preferably, the second display technique is composed of an image display technique displaying projection data obtained by projecting two-dimensionally the image data using a maximum intensity projection technique.

Furthermore, in the diagnostic ultrasound apparatus including the basic constituent, the data producing means may comprise memory means for recording the three-dimensional image data produced in response to the scanning, replay commanding means for making the displaying means display the three-dimensional image data recorded in the memory means, and commanding means capable of commanding, during a replay of the replay, a switchover of a display state of the three-dimensional image data from an image display state on a first display technique suitable for imaging of a blood vessel before injecting the contrast agent to an image display state on a second display state suitable for imaging a blood vessel after start of injecting the contrast agent. This makes it possible to keep on observing images on which blood vessels are distinctly shown all through the periods provided before and after injecting a contrast agent even when images are replayed.

In each foregoing constitution, a harmonic echo technique can be practiced together. To realize this, the signal acquiring means comprises means for passing an only certain frequency component of the echo signal.

Incidentally, the diagnostic ultrasound apparatus according to the foregoing basic constitution may comprise an acquisition unit to acquire an echo signal by scanning a three-dimensional region of an object with an ultrasound beam; a data production unit to produce three-dimensional image data based on the echo signal; a display unit to display the three-dimensional image data; a specifying unit to specify a timing when an ultrasound contrast agent is started to be injected into the object; and a switchover unit to switch over at the specified injection timing a display state of the three-dimensional image data to be displayed by the display unit.

Alternatively as another aspect of the diagnostic ultrasound apparatus according to the present invention, in performing a contrast echo technique with an ultrasound contrast agent injected into the object, the apparatus may comprise switchover controlling means for switching over a display state of the three-dimensional image data displayed by the displaying means between a first display technique used for displaying information about a blood vessel when the echo signal emanated from a tissue of the object is larger in intensity than the echo signal emanated from blood through the blood vessel of the object, and a second display technique used for displaying information about a blood vessel when the echo signal emanated from blood of the blood vessel of the object is larger in intensity than the echo signal emanated from a tissue of the object.

On one hand, in order to accomplish the foregoing object, a method of switching over display of ultrasound images, the comprising the steps of: acquiring an echo signal by scanning a three-dimensional region of an object with an ultrasound beam not only producing three-dimensional image data based on the echo signal but also specifying a timing at which an ultrasound contrast agent is started to be injected into the object; and switching over display states of the three-dimensional image data displayed by display means at a specified timing. Specifically, by way of example, the display states are switched over from a state of projection data of the three-dimensional image data based on a minimum intensity projection technique performed before injecting the ultrasound contrast agent to a state of projection data of the three-dimensional image data based on a maximum intensity projection technique performed after start of injecting the ultrasound contrast agent.

DETAILED DESCRIPTION OF THE PREFERRED EMBODIMENTS

Hereinafter, embodiments of the present invention will now be described with reference to the drawings.

In this embodiment, a diagnostic ultrasound apparatus on a contrast echo technique will be described, in which three-dimensional scanning is performed with an object into which a contrast agent has been injected, so that three-dimensional images are obtained almost in real time.

This diagnostic ultrasound apparatus has, as described below, one feature of automatic and smooth switchovers of display techniques for three-dimensional images between before and after the start of injecting a contrast agent. Specifically, the switchover of these display techniques is realized by switching over projection techniques used to project a three-dimensional image data to a two-dimensional planar. This makes it possible to keep on observing distinctly and finely a region of interest of a three-dimensional image scanned before and after the start of injecting a contrast agent.

Figure 1:
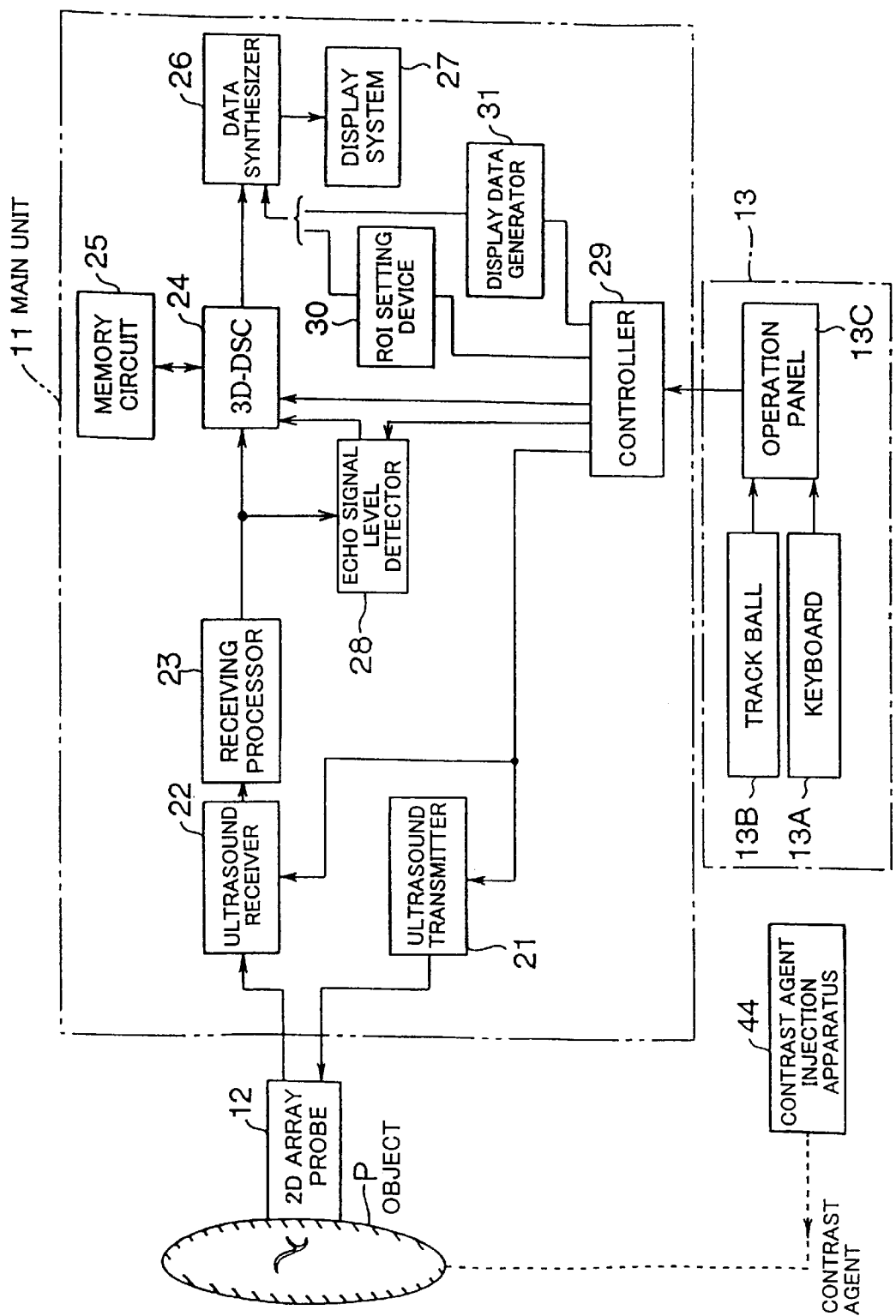
FIG. 1 is a block diagram of a diagnostic ultrasound apparatus according to one embodiment of the present invention.

Referring to FIGS. 1 to 7A and 7B, one embodiment of the diagnostic ultrasound apparatus according to the present invention will be detailed. FIG. 1 outlines the entire configuration of this apparatus.

The diagnostic ultrasound apparatus shown in FIG. 1 is provided with a main unit 11, an ultrasound probe (hereinafter, referred to as a probe) 12 coupled with the main unit 11, and a console 13. An objet to be imaged is denoted by a reference P. A contrast agent injection apparatus 14 used for performing a contrast echo technique is prepared as well.

The console 13 has devices, such as a keyboard 13A, track ball 13B, and operation panel 13C. These operational devices supply to the main unit 11 various types of commands and bits of information given through operator's operations. These commands and bits of information include an item for specifying apparatus conditions, an item for placing a ROI (region of interest) on an image, and an item concerning switchovers of display techniques according to the present invention.

The probe 12, which is a device in charge of transmission and reception of an ultrasound signal to and from the object P, is provided with piezoelectric transducers such as piezoelectric ceramics serving as electric/mechanic reversible conversion elements. One preferred example is a phased array type of probe 12 made such that a plurality of piezoelectric transducers are arranged in a two-dimensional array shape at the tip thereof. Thus the probe 12 converts pulse drive signals, which are given from the main unit 11, to ultrasound pulse signals so as to transmit those signals into the object as one or more ultrasound beams, and converts each of ultrasound echo signals, which are received after having being reflected within the object, to a corresponding echo signal in voltage. The main unit 11 comprises, as shown in the figure, a transmitter 21 and a receiver 22 both coupled with the probe 12, a receiving processor 23 placed at the output side of the receiver 22, a three-dimensional (3D) DSC (digital scan converter) 24, a memory circuit 25, a data synthesizer 26, a display system 27, and an echo signal lever detector 28. Moreover, the main unit 11 has a controller 29, a ROI setting device 30, and a display data generator 31.

First, the transmission and reception system will be described. The transmitter 21 has a pulse generator, a transmission delay circuit, and a pulser, all of which are not shown in the figure. The pulse generator generates, for example, a rate pulse whose rate frequency fr [Hz] is 5 kHz (pulse repetition time is 1/fr [sec]). The rate pulse is distributed to each transmission channel leading to the transmission delay circuit. The circuit receives a timing signal to determine a delay time, which is given to each transmission channel from the controller 29. This allows the transmission delay circuit to provide a commanded delay time to the rate pulse channel by channel. This delay-controlled rate pulse is then supplied to the pulser at each transmission channel. The pulser gives a voltage pulse to each piezoelectric transducer (in each transmission channel) at a time when the rate pulse is received. This causes the probe 12 to radiate ultrasound signals for one or more beam signals. The ultrasound signals transmitted from the ultrasound probe 12 are beam-formed within an object, with their beam directivities set in commanded scanning directions. Temporal intervals of scanning performed by the transmitter 21 are controlled to a predetermined time by means of the controller 29.

Within the object, the ultrasound signals are beam-formed on commanded transmission delay times. The transmitted one or more beam-like ultrasound pulse signals are reflected at places where acoustic impedance is discontinuous. Each reflected ultrasound signal is received and converted into a corresponding voltage-quantity echo signal by the probe 12. This echo signal is fed from the probe 12 to receiver 12 at each reception channel.

The receiver 22 has, in turn from its input side, a pre-amplifier, a reception delay circuit, and an adder, all of which are not shown in the figure. The pre-amplifier comprises amplifier circuits corresponding to the number of reception channels. Also the reception delay circuit comprises delay circuits corresponding to the number of reception channels. Delay times required by the reception delay circuit are given from controller 29 in the form of a delay time pattern signal according to a desired reception directivity. Thus the echo signal is, every reception channel, amplified by the pre-amplifier, subjected to delay time control by the reception delay circuit, and then subjected to addition to the other channel signals by the adder. This addition enhances a signal component reflected in a direction corresponding to the desired directivity. Integrating both transmission and reception directivities determines an entire directivity of a transmitted/received ultrasound beam.

The output end of the adder arranged in the receiver is routed to both of the receiving processor 23 and the echo signal revel detector 28.

The receiving processor 23 comprises, though not shown, a logarithm amplifier, envelope detector, and A/D converter. The receiving processor 23 produces a digital-quantity echo signal in a beam direction to which the reception directivity is given. The resultant echo signal is fed to both 3D-DSC 24 and echo signal level detector 28.

The 3D-DSC 24, which is configured with a read/write circuit having a CPU, inputs echo signals in succession, with successively writing the echo signals at specified addresses of a memory device of the memory circuit 25 as three-dimensional echo data. Thus, three-dimensional volume data composed of image data in a scanned three-dimensional region are stored in the memory.

Moreover, the 3D-DSC 24 has an addition construction that performs, at every predetermined interval, a projecting conversion of the three-dimensional volume data to a two-dimensional planar along a direction viewing from an arbitrary point of view with the use of a maximum intensity projection technique (Max IP technique) or minimum intensity projection technique (Min IP technique). The projection technique used for this projecting conversion is decided based on a command issued from the controller 29.

Further, the 3D-DSC 24 also has a function of reversing luminance gradations of image data responsively to a command outputted from the controller 29.

Since the foregoing projecting conversion produces image data of a two-dimensional projection image, the 3D-DSC 24 reads out those image data in the video format. Namely, by the DSC 24, data composed of signals on raster sequences obtained by ultrasound scanning are converted to two-dimensional image data projecting-converted and mapped in the video format. This image data are then fed to the data synthesizer 26.

On one hand, the controller 29 comprises, by way of example, a computer having a CPU and a memory and sends necessary control signals to constituents of the apparatus in response to signals provided from the console. The control signals include a transmission/reception delay time pattern for beam focusing, a setting signal of ROI (region of interest) to be placed on a display screen, a signal for superposing display information such as scanning parameters on a display screen, a signal with regard to display technique changeovers according to the present invention, a signal indicative of the type of a projection technique, bits of information indicative of whether or not the projection technique involves reversing luminance levels (one of modes 1 to 3 described later), and bits of information indicating a point of view and a viewing direction in projecting a three-dimensional image data. So the output ends of the controller 29 are connected to the transmitter 21, receiver 22, DSC 24, echo signal level detector 28, ROI setting device 30, and display data generator 31.

Figure 2:
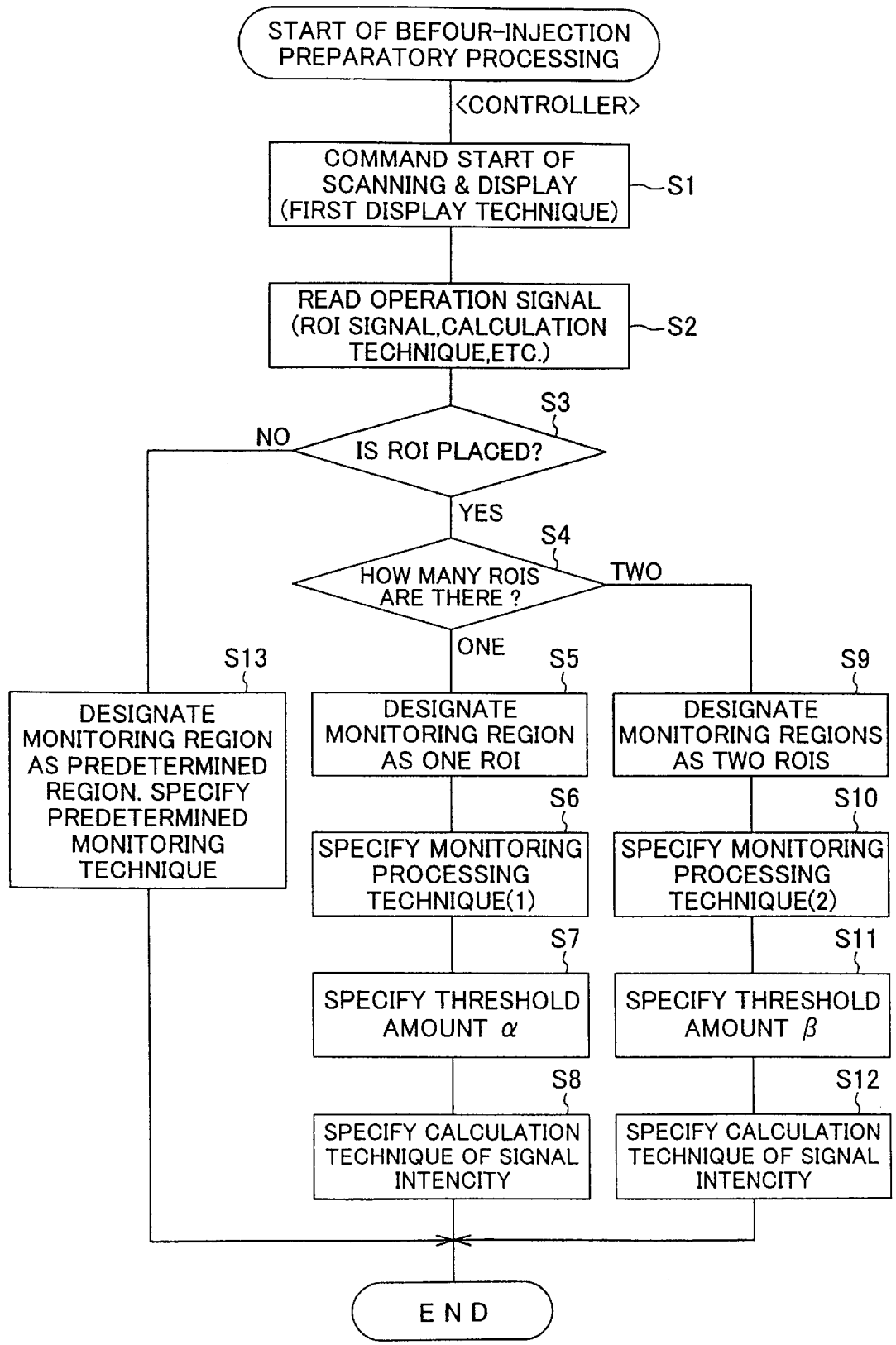
FIG. 2 is an outlined flowchart showing one example of preparation processing performed before injecting a contrast agent, which is executed by a controller.

FIG. 2 shows one example of preparatory processing before injecting a contrast agent, which is performed by the controller 29. The processing in FIG. 2, which realizes part of the features of the present invention, will be detailed later together with examples of monitoring processing (refer to FIGS. 3 and 4) performed by the echo signal level detector 28, the monitoring processing concerning the switchovers of display techniques.

The ROI setting device 30 generates ROI data on the basis of a control signal from the controller 29, and sends the ROI data to the data synthesizer 26. The display data generator 31 generates display data, including a scanning data and time, the name of a patient, a scanned region, and scanning conditions based on control signals from the controller 29, and sends those displayed data to the data synthesizer 26.

The data synthesizer 26 not only superposes the ROI data on the two-dimensional image data (gray-scale image data) sent from the DSC 24 but also combines display data indicative of the scanning parameters with the image data in a superposition or parallel mode, so that one frame of image data is produced.

The image data are read out in sequence by the display system 27. The display system 27 converts the image data into analog-quantity data by an incorporated D/A converter, and visualizes the converted image data as an object's image on an incorporated display such as a TV monitor. Thus, a three-dimensional volume image representing tissue shapes of an object is displayed as a two-dimensional projected image at a frame rate which can be regarded as being in almost real time. With a contrast agent injected, the displayed image provides a contrast echo image in which a state of the contrast agent flowing associated with blood is reflected.

The memory of the memory circuit 25 is constructed such that it is able to memorize image data outputted by the DSC 24 in either or both formats in accordance with raster signal sequences of the ultrasound scanning or the video format. Therefore, the image data can be read out and used in response to an operator's operation after diagnosis. In this case, the image data stored in the memory circuit 25 are fed to the display system 27 via both DSC 24 and data synthesizer 28.

Further, the echo signal level detector 28 is composed of, by way of example, a computer having a CPU and a memory. Alternatively this detector 28 may be possible to be configured by combining digital circuits such as logic circuits. Still alternatively, in the case that the detector is configured with a computer, the detector can use the same hardware as the controller 29 and/or DSC 24, wherein two or three circuits functionally assigned to the above detector, controller, and/or DSC are operated in parallel on such a technique as time sharing.

The echo signal level detector 28 has a function of receiving a digital echo signal outputted by the receiving processor 23, monitoring/determining an intensity of the signal, and giving to the DSC 24 a command of changeovers of "display techniques" (realized by "changeovers of projection techniques") for a three-dimensional image as needed. To be specific, such a function is accomplished by performing processing exemplified in FIGS. 3 and 4.

"A first display technique" prepared in this embodiment, which corresponds to one mode (mode 1), is used for obtaining a displayed state where a three-dimensional volume image is projected and converted into a two-dimensional planar image by using a minimum intensity projection method (Min IP method). The minimum intensity projection method is a technique, along each given viewing line, of selecting a minimum from the intensities (luminance levels) of image data residing along each given viewing line, and projecting an image data representing the selected minimum. This minimum intensity projection technique is effective for display done prior to injecting a contrast agent, that is, a tissue of an object is relatively larger in echo signal intensity than blood flows thereof.

Incidentally, the first display technique includes, as its two modifications, a method of combining the minimum intensity projection technique first carried out and reversal of luminance levels at each pixel carried out after the projection (mode 2), and anther method of reversal of luminance levels at each pixel carried out first and a maximum intensity projection method that follows, which is carried out later (mode 3).

In contrast, "a second display technique" prepared in this embodiment is used for displaying a state where a three-dimensional volume image is projected and converted into a two-dimensional planar image by using a maximum intensity projection method (Max IP method). The maximum intensity projection method is a technique, along each given viewing line, of selecting a maximum from the intensities (luminance levels) of image data residing along each given viewing line, and projecting an image data representing the selected maximum. This maximum intensity projection technique is effective for display done after the start of injecting a contrast agent, that is, blood vessels of an object are relatively larger in echo signal intensity than a tissue thereof.

An ultrasound contrast agent (hereinafter, simply referred to as a contrast agent) is injected into the object by the contrast agent injection apparatus 14, which is installed separately from this diagnostic ultrasound apparatus. The contrast agent, which consists of, for example, 5%-diluted human albumin essentially containing microbubbles produced manually or by using a sonicator, shows an intensity enhancement effect when scattering ultrasound signals radiated thereon. Particularly, a scattering characteristic of the microbubbles against the ultrasound signal is non-linear, which causes a scattered signal to include higher-intensity non-fundamental signal components such as $2^{nd}$ harmonics. The contrast agent is injected into the object P by the injection apparatus 14 with a trans-venous or trans-arterial injection technique.

The operations and advantages of this embodiment will now be described with centering on switchover control of the image display techniques. In this embodiment, a contrast echo technique is to be performed.

Figure 3:
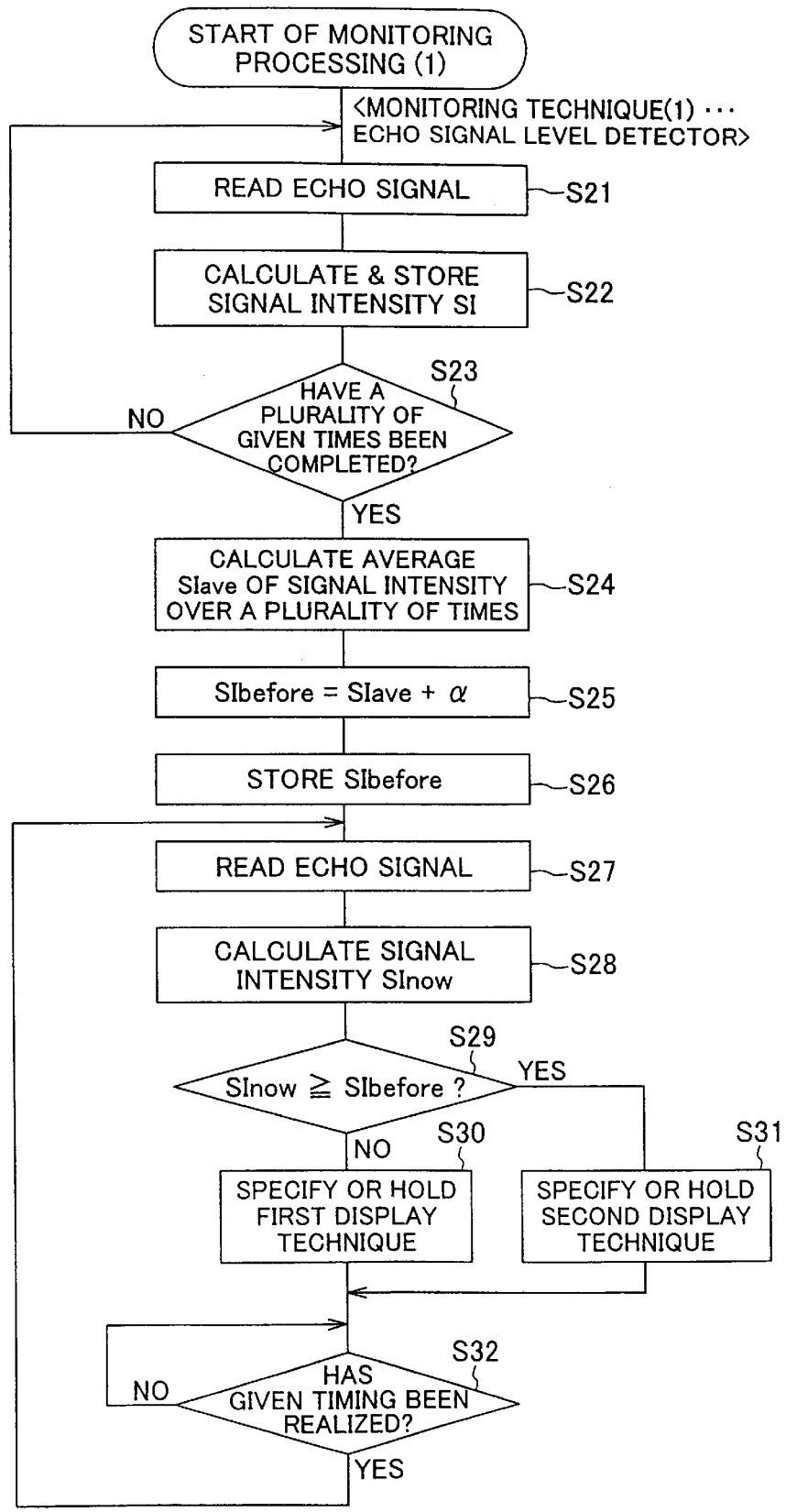
FIG. 3 shows an outlined flowchart exemplifying a monitoring processing technique (1) executed by an echo signal level detector.
Figure 4:
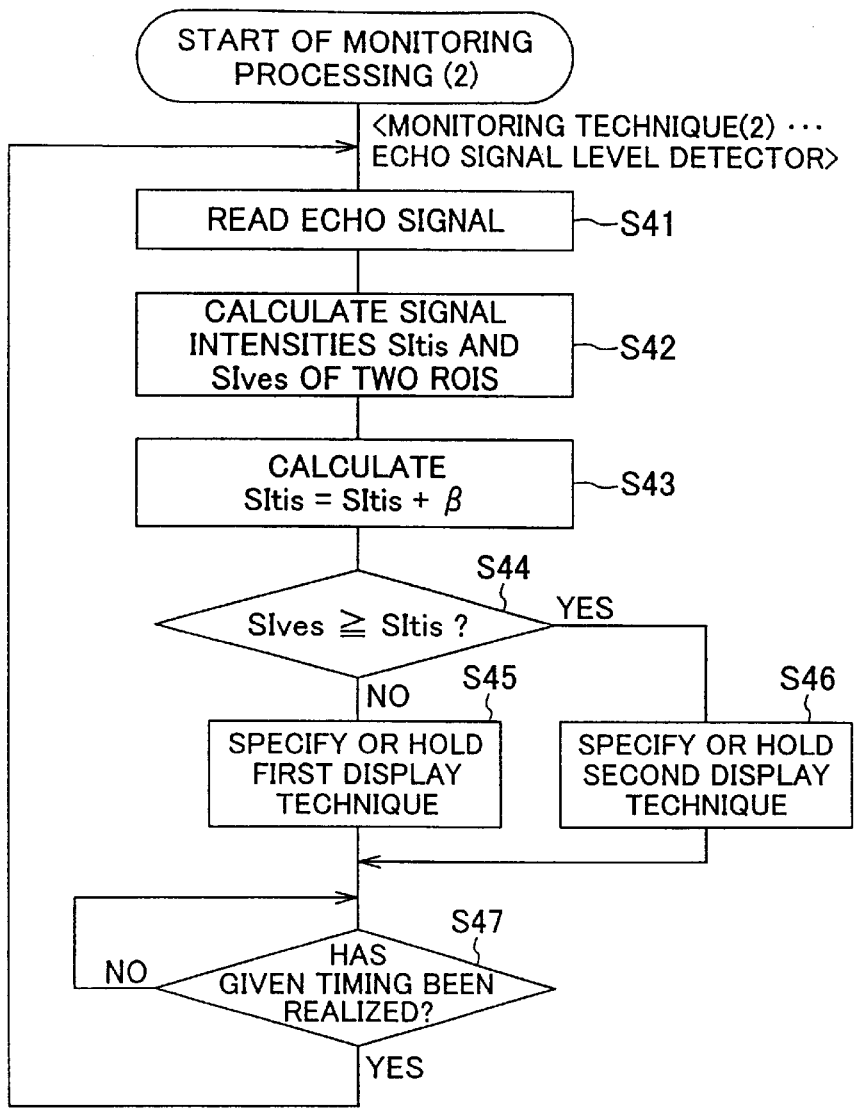
FIG. 4 shows an outlined flowchart exemplifying a monitoring processing technique (2) executed by an echo signal level detector.

FIG. 2 shows preparatory processing conducted before the injection of a contrast agent, which is performed by the controller 29. FIGS. 3 and 4 show monitoring processing performed by the echo level detector 28 responsively to a result of the preparatory processing. The monitoring processing (1) shown in FIG. 3 and the monitoring processing (2) shown in FIG. 4 are selected alternatively and performed.

The controller 29 performs the preparatory processing shown in FIG. 2 at given timing before injecting a contrast agent.

First, the controller 29 commands the start of scanning on a desired mode and the display of images obtained by the scanning (step S1). This image display is processing necessary to specify a monitoring region for monitor the injection of a contrast agent, so that a technique of displaying the images is specified as one default condition into the first display technique (mode 1) (namely, a projecting conversion on the Min IP technique). This makes it possible that, by performing the projecting conversion on the Min IP technique, a three-dimensional image acquired on, for example, a convex scan is displayed in almost real time as a planar image $IM_{initial}$ exemplified by FIG. 5A or 6A. As needed, as the first display technique, the mode 2 or 3 may be specified.

The controller 29 then reads an operated signal from the console 13 and interprets the signal (step S2). This operation signal includes pieces of information required to detect an increase in echo signal level showing the start of injecting a contrast agent (precisely, a timing when the contrast agent begins to arrive at a region to be scanned after a certain delay from an actual injection), the information containing ROI setting information, a signal representing the type of a calculation method of signal intensity, and a threshold α or β used for comparison of signal intensities.

The controller 29 determines whether or not an operator desires to set a ROI based on contents represented by the operational signal (step S3). Generally, since it is advantageous to use the only pixels present in a ROI as objectives to detect an increase in intensity (luminance) in terms of accuracy of the detection, a routine for setting the ROI is required.

If YES at this determination, that is, it is determined that the ROI is set as a monitoring region to decide a timing at which a contrast agent is started to be injected, it is then determined by the controller 29 that the number of ROIs to be set is one or two (step S4). Alternatively, three or more ROIs can be placed on the same single image screen. In this embodiment, two ROIs are adopted as representatives for a plural of ROIs.

When it is determined at the above determination that the ROI setting number is one, processing shown at steps S5 to S8 is performed in sequence. Specifically, the operator places one ROI on a blood vessel B in an image $IM_{initial}$ as exemplified in FIG. 5A (step S5). Normally, this single ROI is placed on objects such as a relatively large blood vessel or a cardiac cavity in order to sense a more distinct increase in luminance. Any shape of the ROI is available, but it is preferred that the shape contains as wider region of the blood vessel B as possible (for example, a circular, elliptic, or rectangular shape). Information about the position and shape of this ROI is fed to the echo signal level detector 28.

Responsively to specifying the ROI setting number is one, a monitoring processing technique used by the echo signal level detector 28 is then specified into the monitoring processing technique =(1) (step S6). This monitoring processing technique (1) is realized by processing shown in FIG. 3, and detects the injected contrast agent at a region to be scanned on the basis of temporal sequential changes in echo signal intensity itself acquired from the same ROI placed on the blood vessel, as exemplified in FIG. 5A.

A threshold a is then specified according to the operational information, and notified to the echo signal level detector 28 (step S7). This threshold a is an amount to detect a situation where it is recognized that the contrast agent begins to be injected, depending on how much the signal intensity increases from a signal intensity $SI_{ave}$ that is a reference predetermined sequentially in time (refer to FIG. 5B). The threshold α is set to an appropriate amount that is not influenced by noise and others.

A technique of calculating signal intensity is then specified based on operational information, and notified to the echo signal level detector 28 (step S8). This calculation technique determines that the calculation should be done on either a total sum or an average of the values (signal intensities) of pixels falling in the ROI.

Monitoring of the echo signal intensity is then handed to the echo signal level detector 28, where the monitoring processing technique (1) shown in FIG. 3 is performed as described later.

Meanwhile, when it is determined at step S4 that the ROI setting number is two, a series of steps of processing shown at steps S9 to S12 are performed in sequence. Specifically, the operator places two ROIs: ROI1 and ROI2 on a blood vessel B and a tissue T respectively in an image $IM_{initial}$ as exemplified in FIG. 6A (step S9). Information about the positions and shapes of those ROIs: ROI1 and ROI2 is fed to the echo signal level detector 28.

Responsively to specifying the ROI setting number is two, a monitoring processing technique used by the echo signal level detector 28 is then specified into the monitoring processing technique (2) (step S10). This monitoring processing technique (2) is realized by processing shown in FIG. 4, and detects the injected contrast agent at a region to be scanned on the basis of comparison made between echo signal intensities acquired from the two ROIs placed on both tissue and blood vessel, as exemplified in FIG. 6A.

A threshold β is then specified according to the operational information, and notified to the echo signal level detector 28 (step S11). This threshold β is an amount to exclude fluctuations due to noise components or others when making a comparison between a signal intensity $SI_{ves}$ of a blood flow and a signal intensity $SI_{tis}$ of a tissue. In this embodiment, the threshold β is designated to an appropriate amount, which is added to the signal intensity $SI_{tis}$ of the tissue (refer to FIG. 6B).

Like the foregoing step S8, a technique of calculating signal intensity is then specified based on operational information, and notified to the echo signal level detector 28 (step S12).

Monitoring of the echo signal intensity is then handed to the echo signal level detector 28, where the monitoring processing technique (2) shown in FIG. 4 is performed as described later.

Incidentally, if it is determined at the foregoing step S3 that the ROI setting is not desired, a region to be monitored of the signal intensity is specified as, for example, an entire image on which a scanned region is projected, to perform a given monitoring processing is notified to the echo signal level detector 28 on the basis of a sum or an average of the signal intensities of pixels consisting of the entire image, and this preparatory processing is completed (step S13).

In response to this notification, the detector 28 detects a timing at which such sum or average value of the signal intensities begins to go up, and, at the timing, sends to the DSC 24 a signal representing that the contrast agent starts. As a result, the DSC 24 allows, through the data synthesizer 26, the display system 27 to display a planar image switched over from the first display technique which has been used so far to the second display technique (that is, the maximum intensity projection technique).

As an alternative way, this detection processing can be changed to a configuration in which a sum or an average of the signal intensities acquired from an entire. three-dimensional scanning region is calculated, and at a temporal instant when this calculated value starts to rise is recognized as the start of an injection of a contrast agent at a region to be scanned.

Referring to FIG. 3, the monitoring processing technique (1) will now be described. The echo signal level detector 28 executes this processing.

Figure 5A:
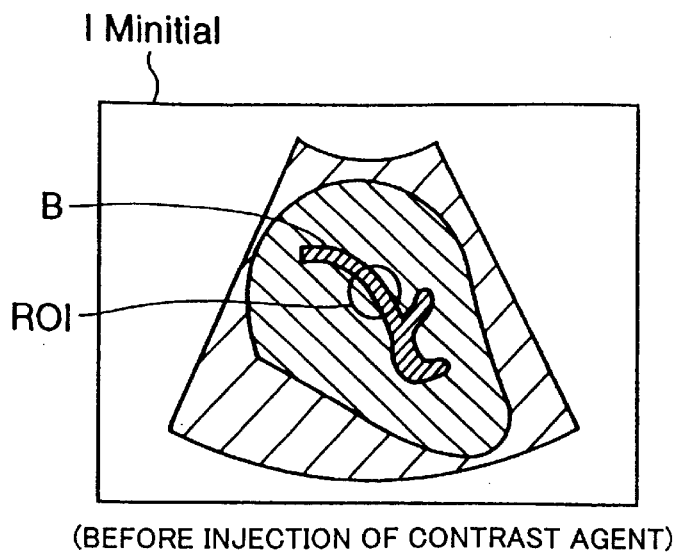
FIGS. 5A and 5B are explanations of both of a single ROI placed as a monitoring region on a screen before injecting the contrast agent and a threshold used for determining an increase in intensity of an echo signal.
Figure 5B:
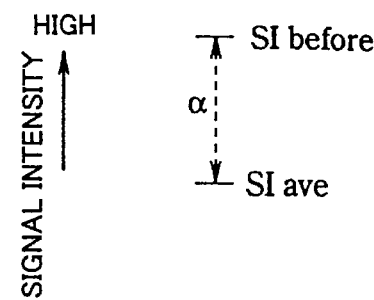
Figure 6A:
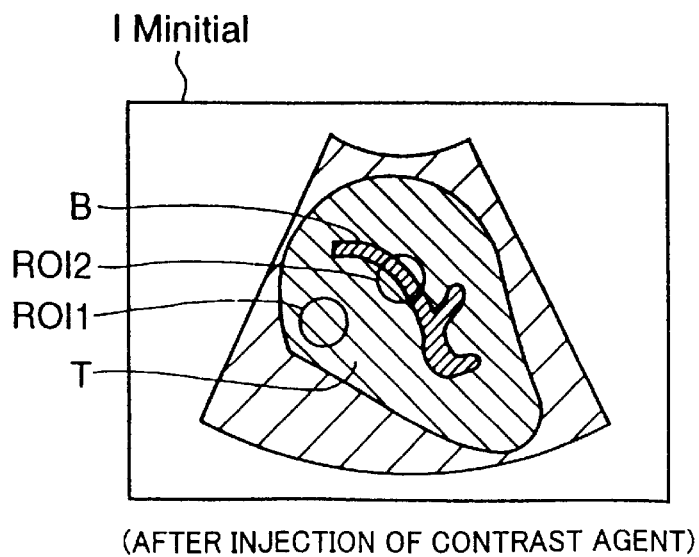
FIGS. 6A and 6B are explanations of both of two ROIs placed as monitoring regions on a screen before injecting the contrast agent and a threshold used for determining an increase in intensity of an echo signal.
Figure 6B:
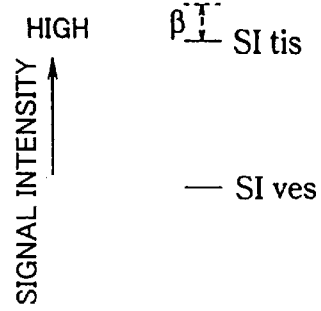

The detector 28 reads an intensity of each pixel (i.e., an intensify of each echo signal) falling within a region specified by the ROI shown in FIG. 5A, from image data sent from the receiving processor 23, calculates a signal intensity SI on the specified calculation technique (the sum or average), and memorizes it (step S21, S22). In this calculation and storage, an alternative way is that pixels falling within the ROI on the planar image IMinitial shown in 5A are traced back to corresponding positions in the original three-dimensional image data, and intensities of the traced corresponding pixels in the three-dimensional image data are read, calculated and stored. The calculation and storage at steps S21 and S22 are repeated a given number of times (step S23). Alternatively, this processing may be confined to one time of calculation.

The detector 28 then averages the signal intensities SI calculated a plurality of times of repetitions before obtaining an average intensity $SI_{ave}$ (step S24). Further, using this average intensity $SI_{ave}$, an expression of $SI_{before}=SI_{ave}+\alpha$ is calculated and stored (steps S25, S26). The amount of $S_{before}$ becomes an echo signal intensity of blood flow that should be a reference at a certain temporal instant before injecting a contrast agent into a region to be scanned. This means that all echo signal intensities $SI_{now}$ of blood flow that will be detected after the injection at a region to be scanned are compared to the reference intensity $SI_{before}$.

In order to make comparison, like the step S21, the detector 28 reads image data derived from the pixels within the ROI, i.e., echo signals, and calculates a signal intensity $SI_{now}$ on the specified calculation technique (steps S27, S28). Then, it is determined by the detector whether or not $SI_{now} \geq SI_{before}$ is realized (step S29).

When it is determined at the above largeness comparison that $SI_{now} < SI_{before}$ is sustained (NO at step S29), it is recognized that a contrast agent has not been injected yet (or a contrast agent has not reached a region to be scanned yet, though an actual injection has already been done), and a command for holding the first display technique that has been used so far is issued (step S30). This permits the echo signal level detector 28 to issue to the DSC 24 a command of holding the minimum intensity projection technique corresponding to a mode 1 of the display technique.

Therefore, blood vessels are depicted before injecting a contrast agent on the basis of the projecting conversion that enhances an echo signal of a blood vessel normally lower in echo signal intensity than organ tissues.

On one hand, when YES at the determination at Step S29, that is, the condition of $SI_{now} \geq SI_{before}$ is fulfilled, the intensity of an echo signal from a blood vessel reaches a given amount or more. Thus, the detector 28 recognizes that a contrast agent that was injected begins to arrive at a region to be scanned (i.e., the start of an effective injection of the contrast agent). Responsively to this, the detector 28 issues to the DSC 24 a command of performing the maximum intensity projection technique in order to change over the display techniques from the first display technique (mode 1) to the second display technique (step S31).

As a result of it, the technique of depicting a blood vessel is automatically switched over to that suitable for a technique used after the start of injecting the contrast agent into a region to be scanned. The technique is based on a projecting conversion enhancing an echo signal from a blood vessel, which has usually become higher in intensity than that from an organic tissue due to the enhancement of intensity of scatted ultrasound waves resultant from the contrast agent. The second display technique is maintained, provided that the contrast agent is kept to reach the scanned region thereafter.

Thus, depending on if the condition of $SI_{now} \geq SI_{before}$ is fulfilled or not, the first or second display technique is instructed or maintained. Then, the processing is returned to step S27 after waiting for a certain period of time, before a series of processes described above are repeated (step S32).

Furthermore, the monitoring processing technique (2) shown in FIG. 4 will now be described. The echo signal level detector 28 also executes this processing. Either of the monitoring processing techniques (1) or (2) are selected.

The detector 28 reads an intensity of each pixel (i.e., an intensify of each echo signal) falling within each of two regions specified by the two ROIs: ROI1 and ROI2 shown in FIG. 6A, from image data sent from the receiving processor 23, calculates signal intensities $SI_{tis}$ and $SI_{ves}$ for the individual ROIs on the specified calculation technique (the sum or average), and memorizes them (step S41, S42). In this calculation and storage, an alternative way is that pixels falling within each of the ROI1 and ROI2 on the planar image IMinitial shown in 6A are traced back to their corresponding positions in the original three-dimensional image data, and intensities of the traced corresponding pixels in the three-dimensional image data are read, calculated and stored. A signal intensity from the ROI1 placed on the tissue expressed by $SI_{tis}$ and that from the ROI2 placed on the blood vessel expressed by $SI_{ves}$.

Using these signal intensities $SI_{tis}$ and $SI_{ves}$, the detector 28 then calculates an expression of $SI_{tis}=SI_{tis}+\beta$ and memorizes its calculated result (step S43). This calculated tissue signal intensity $SI_{tis}$ provides an intensity of an echo signal that should be compared to an echo signal echo $SI_{ves}$ from a blood vessel. In other words, the intensity $SI_{tis}$ is used to make a comparison between the echo signal intensity $SI_{ves}$ of a blood vessel and the echo signal intensity $SI_{tis}$ of a tissue in order to recognize the start of injecting a contrast agent at a region to be scanned at a temporal instant when the former becomes equal to the latter in intensity.

The detector 28 then determines whether or not a condition of $SI_{ves} \geq SI_{tis}$ is realized (step S44). When it is determined at the largeness comparison that $SI_{ves} < SI_{tis}$ is found (NO at step S44), it is recognized that a contrast agent has not been injected yet (or a contrast agent has not reached a region to be scanned yet because of a certain delay, though an actual injection has already been done), and a command for holding the first display technique that has been used so far is issued (step S45). This permits the echo signal level detector 28 to issue to the DSC 24 a command of holding the minimum intensity projection technique corresponding to a mode 1 of the display technique.

Therefore, like the monitoring processing technique (1), blood vessels are depicted before injecting a contrast agent on the basis of the projecting conversion that enhances echo signals of blood vessels lower in intensity than organic tissues.

On one hand, when YES at the determination at Step S44, that is, the condition of $SI_{ves} \geq SI_{tis}$ is fulfilled, the detector 28 recognizes that a contrast agent that was injected begins to arrive at a region to be scanned (i.e., the injection start of the contrast agent at a region to be scanned). Responsively to this, the detector 28 issues to the DSC 24 a command of performing the maximum intensity projection technique in order to change over the display techniques from the first display technique (mode 1) to the second display technique (step S46).

As a result of it, similarly to the monitoring processing technique (1), the technique of depicting a blood vessel is automatically switched over to that suitable for a technique used after the start of an injection of the contrast agent. The technique is based on a projecting conversion enhancing an echo signal from a blood vessel, which has become higher in intensity than that from an organic tissue due to the enhancement of intensity of scatted ultrasound waves resultant from the contrast agent. The second display technique is maintained, provided that the contrast agent is kept to reach the scanned region thereafter.

Thus, depending on if the condition of $SI_{ves} \geq SI_{tis}$ is fulfilled or not, the first or second display technique is instructed or maintained. Then, the processing is returned to step S27 after waiting for a certain period of time, before a series of processes described above are repeated (step S47).

Thus, then intensity of the echo signal is monitored at any time, and the display technique of the three-dimensional image is switched over from the first display mode (any one of the modes 1 to 3) to the second display mode in an automatic fashion.

Figure 7A:
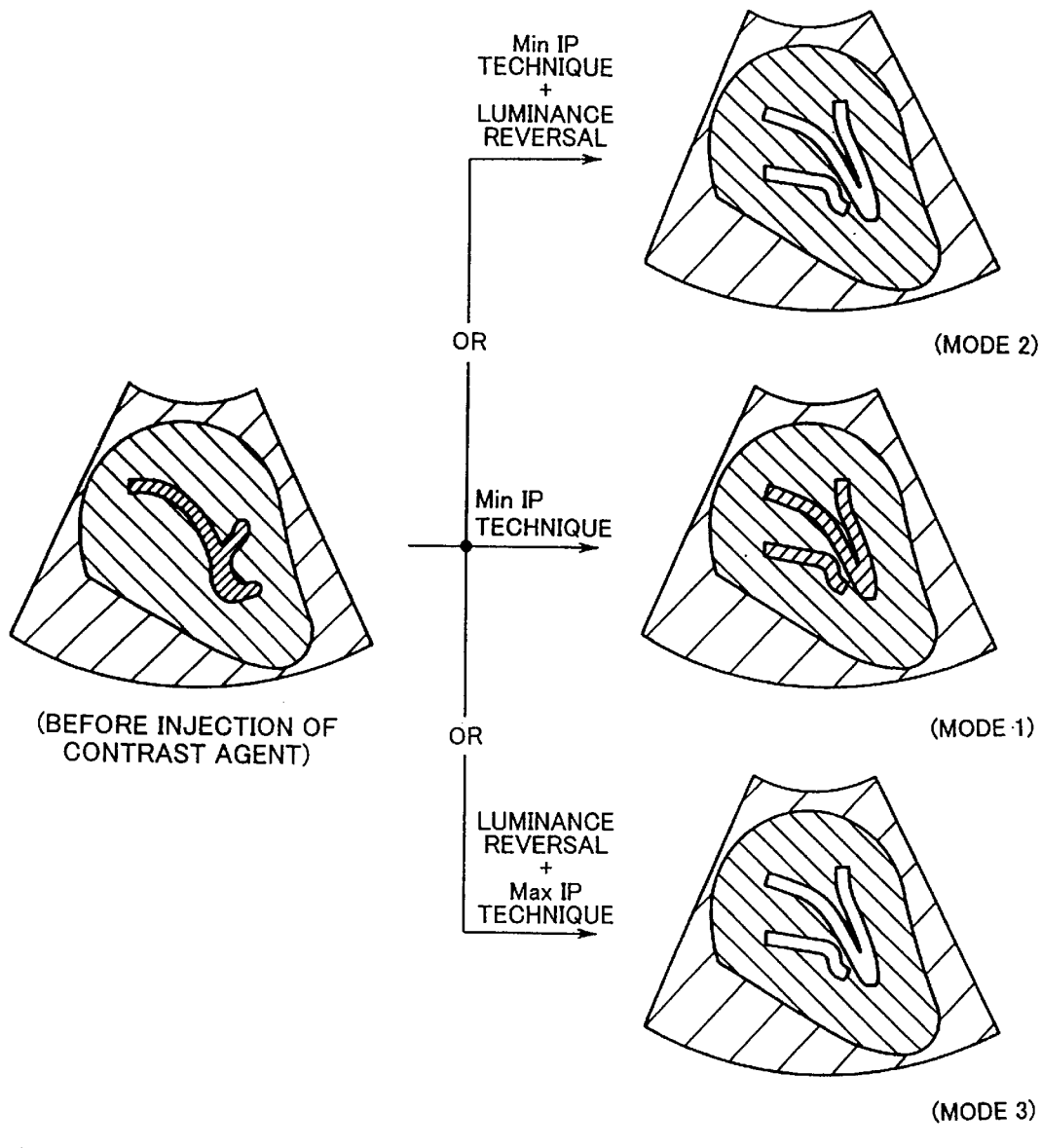
FIGS. 7A and 7B explain, respectively, images on a first and second display techniques used before and after the start of injecting the contrast agent.

Namely, in an echo image acquired before injecting a contrast agent, the luminance of an echo of an organic tissue is relatively higher and that of blood flowing through a vessel is lower. Nevertheless, the present embodiment enables a large blood vessel system to be visualized distinctly thanks to the first display technique, i.e., the minimum intensity projection technique, as shown in FIG. 7A. In general, it is frequent that an examiner or a doctor searches a cross section effective for diagnosis utilizing a relatively large blood vessel system as a landmark. For such section search, the foregoing operation becomes securer and easier, because of a more distinct display of such a blood vessel.

In addition, selecting the mode 2 or 3 involving the luminance reversal makes it possible to diversify display of blood vessels.

Figure 7B:
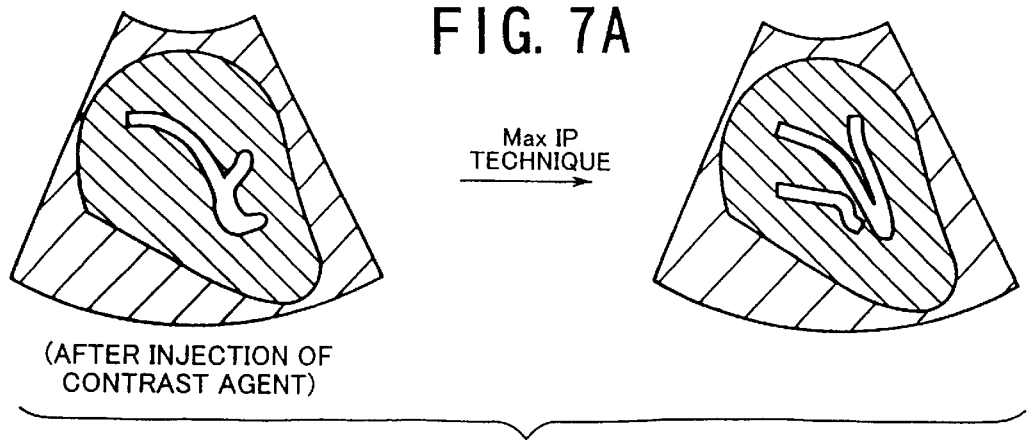

In contrast, in most cases, levels of echo signals are reversed between an organic tissue and a blood vessel system after the injection of a contrast agent, since the contrast agent passes through the vessel. Therefore, in the present embodiment, as shown in FIG. 7B, the display technique is automatically switched over to the second display technique, namely, the maximum intensity projection technique in synchronism with an injection of the contrast agent into a region to be scanned. This results in a secure depiction of the blood vessel system contained in three-dimensional image information.

Accordingly, due to the fact that attention is paid to display of a blood vessel system continuously though a state in which a contrast agent has not been injected yet to the following state in which the contrast agent is now under injection, a more continuos and secure trace can be made between images produced before the injection to images produced after the start of the injection, thus necessary information on the blood vessel being provided.

Moreover, it is enough for an operator to operate the contrast agent injection apparatus 14 so as to commence the injection when carrying out the contrast echo technique, which reduces an operational amount. Further, an operator is not required to worry about, during his or her operation, whether a blood vessel system is securely depicted or not, thus providing a secondary merit that the operator is set free from such an annoying operation.

In the present embodiment, the controller 29, transmitter 21, probe 21, receiver 22, and receiving processor 23 constitute signal acquiring means of the present invention; part of the functions of the 3D-DSC 24 and the memory circuit 25 constitute data producing means of the present invention; and the data synthesizer 26 and the display system 27 constitute display means of the present invention. Moreover, part of the functions of each of the controller 29 and the echo signal level detector 28 and the console 13 compose injection timing specifying means of the present invention, while another part of the functions of the echo signal level detector 28 and part of the functions of the DSC 24 compose display switchover means.

In addition, various modifications of the diagnostic ultrasound apparatus according to the foregoing embodiment will now be provided as follows.

Figure 8:
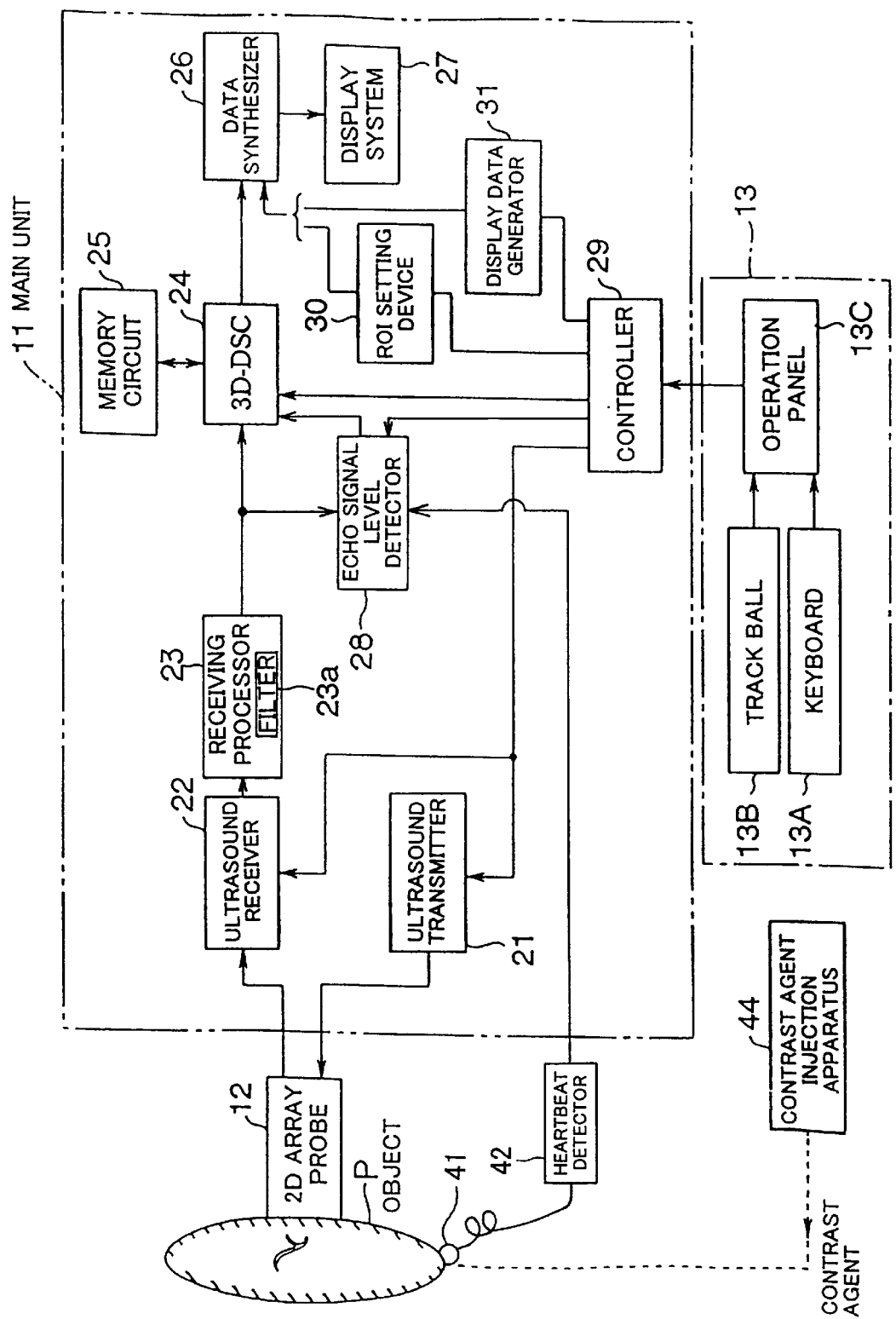
FIG. 8 shows a block diagram of a diagnostic ultrasound apparatus according to one modification of the present invention.

As an example, in the case of adopting an organ that moves largely, such as the heart, as an object to be scanned, an echo signal level may be averaged over several heartbeat cycles to monitor an increase in its level. To accomplish the average using the heartbeat cycles, one example is shown in FIG. 8 wherein a configuration to detect an ECG signal is installed. Specifically, an ECG sensor 41 and a heartbeat detector 42 are installed. The ECG sensor 41, which is contacted to the body surface of an object P, is used for acquire an ECG signal of the object. The heartbeat detector 42 receives the ECG signal supplied from the ECG sensor 41, produces a trigger signal synchronized with the heartbeat cycles, and feeds the trigger signal to the echo signal level detector 28. In synchronism with the trigger signal, the detector 28 performs calculation for the average of echo signal levels. Thus, the echo signal levels can be averaged with the heartbeat cycles, so that the injection of a contrast agent can be detected with high stability even when organs that show a large amount of motion.

As another example is such that a threshold level to sense an increase in echo signal intensity can be adjusted into any level, as needed. This threshold is a parameter exemplified as the threshold a described in FIG. 5B (refer to the processing in FIG. 3). For example, in the configuration of FIG. 8, this threshold a is set to an amount, which is realized by raising a luminance level averaged over one cycle of heartbeats, by 4 decibels than its constant level obtained before the injection. This means for adjusting the threshold can be obtained if configured such that an operator gives the controller 29 a desired threshold level through the console 13.

Figure 9:
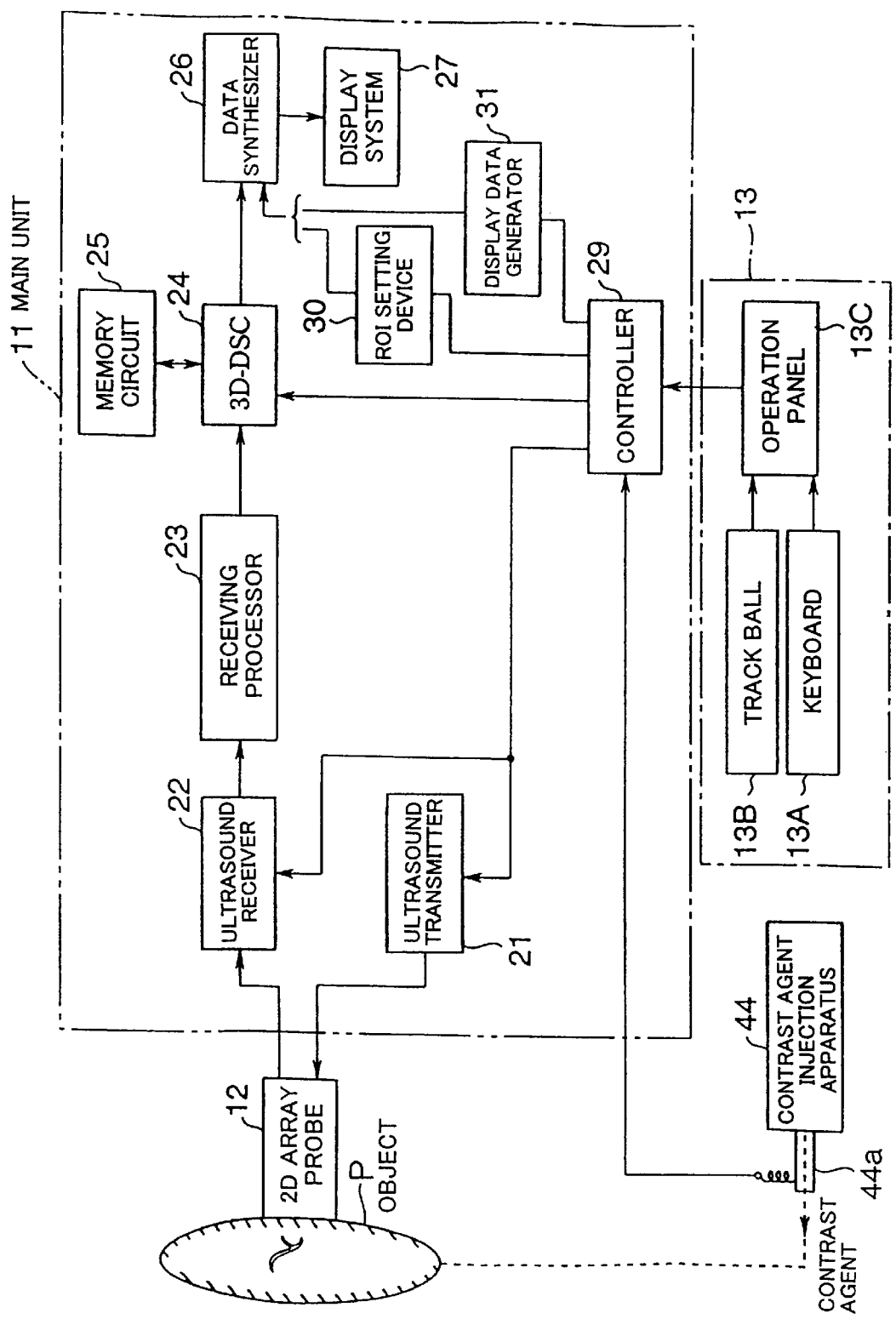
FIG. 9 shows a block diagram of a diagnostic ultrasound apparatus according to another modification of the present invention.

Furthermore, the means for determining injection timing of a contrast agent may be modified into a configuration incorporated into a diagnostic ultrasound apparatus shown in FIG. 9. A contrast agent injection apparatus 44 is electrically combined with the diagnostic ultrasound apparatus. The injection apparatus 44 has a syringe 44a to inject a contrast agent. The syringe 44a is configured to automatically provide a start signal to the controller 29, when its cylinder begins to be pushed down for injection. The controller 29 receives the start signal, waits for a certain period of time for delay, and sends a display switchover signal to the DSC 24. This is able to automatically switch over a blood vessel image displayed with the first display technique to that displayed with the second display technique, under the contrast echo imaging on three-dimensional scanning, thus providing similar operations and advantages to those described before. In this example, there is no need to have the echo signal level detector that was arranged in the foregoing embodiments.

In the foregoing embodiment and modifications, the means for determining the contrast agent injection timing have a constitution to automatically determine the injection timing, but the constitution may be replaced by a manually operated one capable of notifying the diagnostic ultrasound apparatus of the injection timing responsively to an operator's operation. As observing images acquired before the injection of a contrast agent, the operator operates, for example, the keyboard 13A of the console 13 at an appropriate time so that its operated timing is sent to the DSC 24 via the controller 29, providing the manually operated constitution.

Furthermore, the contrast echo technique according to the present invention can be carried out together with harmonic imaging. In the case of performing the harmonic imaging, it is enough that the receiving processor 23 of the diagnostic ultrasound apparatus has a bandpass filter 23a passing an only specified frequency component of a transmission frequency of an ultrasound signal (for example, twice the transmission frequency) (refer to FIG. 8). It is generally known that an echo signal reflected by a contrast agent harmonics, such as twice, triple, etc. a transmission frequency, at a relatively larger proportion that that from an organic tissue. Monitoring the signal intensity on an echo signal composed of the harmonic component enables a highly sensitive detection of a signal inherent to the contrast agent, thus making it possible to determine timing of the contrast agent injection with high precision. Incidentally, in the case that an A/D converter is inserted in the upper stage of the receiving processor 23, or in the case that a digital type of circuitry is adopted by an A/D converter inserted in the upper side of the entire receiving/processing system, the foregoing filter 23a is composed of a digital filter.

Still, another modification may be provided by a constitution where the memory device of the memory circuit 25, which is placed to store three-dimensional image information, memorizes image data that underwent a projecting conversion on the first or second display technique, and the memorized image data are simply replayed after scanning, as needed. Even when being replayed, this helps an observer observe continuously blood vessel images obtained before and after the start of injecting a contrast agent.

Alternatively, image data that has not experienced a projection conversion can be stored, without any processing involved, in the memory device of the memory circuit 25 and an operator is able to appropriately specify either the minimum or maximum intensity projection technique in the repay of those image data.

On one hand, the foregoing embodiment and its modifications adopts the constitution where the two-dimensional array probe 12 is used for three-dimensional scanning, but one-dimensional phased array probe can also be used. In such a case, the one-dimensional probe may be spatially moved by hand along the object body surface for scanning, during which period moved positions of the probe is detected by a positional detector. On the basis of the spatial positional information, a three-dimensional scan data consisting of a plurality of section data are arranged in a memory at an adequate spatial interval set so as to avoid data superposition.

The foregoing embodiment and its modifications are only providing the representative constitutions in which the present invention is practiced and do not mean that the scope of the present invention is limited to those constitutions. The scope of the present invention should be derived from the concepts described in the claims. For a person skilled in the art, diagnostic ultrasound apparatuses according to a variety of other modifications can be conceivable without departing from the scope of the present invention.

As described so far, a timing when an ultrasound contrast agent is injected into a region to be scanned of an object is specified and display states of three-dimensional image data to be displayed by display means are switched over at the specified injection timing. For instance, the display changeovers are done such that before the injection, the image data is projected to be displayed on a minimum intensity projection technique, while after the injection, the image data is projected to be displayed on a maximum intensity projection technique. Therefore, under the performance of contrast echo imaging involving a contrast agent on three-dimensional scanning, displayed images always provide securely depicted blood vessels in both periods before and after an injection of the contrast agent. Thus, the vessels can be observed continuously, thereby contributing to an improvement in diagnosis performance and lessening an operational burden on operators.

What is claimed is:

1. A diagnostic ultrasound apparatus comprising:

signal acquiring means for acquiring an echo signal by scanning a three-dimensional region of an object with an ultrasound beam;

data producing means for producing three-dimensional image data based on the echo signal;

displaying means for displaying the three-dimensional image data;

specifying means for specifying a timing at which injecting an ultrasound contrast agent into the object is started; and display switchover means for switching over at the specified timing a display state of the three-dimensional image data displayed by the displaying means, wherein the specifying means is composed of means for automatically specifying the injection timing as the ultrasound contrast agent is injected, the specifying means has setting means for setting the injection timing from the echo signal itself, and the displaying means is means for displaying projection data obtained by projecting two-dimensionally the three-dimensional image data with a desired projection technique and the display switchover means is means for switching over the projection technique at the projection timing specified by the specifying means.

2. A diagnostic ultrasound apparatus comprising:

an acquisition unit configured to acquire an echo signal by scanning a specified three-dimensional region of an object with an ultrasound beam;

a data production unit configured to produce three-dimensional image data based an the echo signal;

a processing unit configured to produce two-dimensional image data from the three-dimensional image data using a specified processing technique;

a display unit configured to display the two-dimensional image data;

a specifying unit configured to specify a timing when an ultrasound contrast agent that has been injected into the object begins to arrive at the three-dimensional region; and a switchover unit configured to switch the processing technique at the specified injection timing.

3. The diagnostic ultrasound apparatus of claim 2, wherein the specifying unit is configured to automatically specify the timing after the ultrasound contrast agent has been injected into the object.

4. The diagnostic ultrasound apparatus of claim 3, wherein the specifying unit is configured to automatically specify the timing responsive to a signal given by a contrast agent injection apparatus used to inject the contrast agent.

5. The diagnostic ultrasound apparatus of claim 3, wherein the specifying unit is configured to set the specified timing based on the echo signal itself.

6. The diagnostic ultrasound apparatus of claim 5, wherein the specifying unit has at least one of a first comparing element configured to specify the specify timing by making a comparison in strength between the echo signal emanated from a tissue of the object and the echo signal emanated from a blood flow thereof and a second comparing element configured to specify the specified timing by making a comparison in strength between echo signals emanated from a blood flow of the object at two sequential timings.

7. The diagnostic ultrasound apparatus of claim 6, wherein the first and second comparing elements are configured to perform the comparison using either a sum and an average of intensity of at least part of the echo signal providing three-dimensional image data.

8. The diagnostic ultrasound apparatus of claim 6, wherein the first and second comparing elements are configured to perform the comparison using either a sum and an average of signal intensities of a group of signals constituting at least part of signals made up of the echo signal acquired at every spatial position in the three-dimensional region.

9. The diagnostic ultrasound apparatus of claim 6, wherein the first and second comparing elements are configured to perform the comparison using either a sum and an average over a certain period of time with respect to signal intensities of a group of signals constituting at least part of signals made up of the echo signal acquired at every spatial position in the three-dimensional region.

10. The diagnostic ultrasound apparatus of claim 2, wherein the switchover unit is configured to switch a first display technique used as the processing technique before the ultrasound contrast agent arrives at the three-dimensional region to a second display technique used as the processing technique after the ultrasound contrast agent begins to arrive at the three-dimensional region.

11. The diagnostic ultrasound apparatus of claim 10, wherein the first display technique is configured to project the three-dimensional image data using a minimum intensity projection technique so that projected image data serving as the two-dimensional image data are produced and to display the projected image data.

12. The diagnostic ultrasound apparatus of claim 10, wherein the first display technique is configured to project the three-dimensional image data using a minimum intensity projection technique so that projected image data serving as the two-dimensional image data are produced, to reverse the projected image data in luminance gradations so that reversed projected image data are produced, and to display the reversed projected image data.

13. The diagnostic ultrasound apparatus of claim 10, wherein the first display technique is configured to reverse the produced three-dimensional image data in luminance gradations so that reversed three-dimensional image data are produced, to project the reversed three-dimensional image data using a maximum intensity projection technique so that projected image data serving as the two-dimensional image data are produced, and to display the projected image data.

14. The diagnostic ultrasound apparatus of claim 10, wherein the second display technique is configured to project the three-dimensional image data using a maximum intensity projection technique so that projected image data serving as the two-dimensional image data are produced and to display the projected image data obtained.

15. The diagnostic ultrasound apparatus of claim 2, wherein the processing unit is configured to project the three-dimensional image data to the two-dimensional image data using a specified projection technique serving as the specified processing technique and the switchover unit is configured to switch the projection technique at the specified injection timing.

16. A method of switching display of ultrasound images, comprising the steps of:
acquiring an echo signal by scanning a three-dimensional region of an object with an ultrasound beam;
producing three-dimensional image data based on the echo signal;
producing two-dimensional image data from the three-dimensional image data using a specified processing technique;
displaying the two-dimensional image data;
specifying a timing at which an ultrasound contrast agent that has been injected into the object begins to arrive at the three-dimensional region; and
switching the processing technique at the specified timing.

17. The display switching method of claim 16, wherein, at the switching step, the processing technique is switched over from a minimum intensity projection technique performed on the three-dimensional image data before the ultrasound contrast agent arrives at the three-dimensional region to a maximum intensity projection technique performed on the three-dimensional image data after the ultrasound contrast agent begins to arrive at the three-dimensional region.

18. The display switching method of claim 16, wherein, at the specifying step, the timing is automatically specified after the ultrasound contrast agent has been injected into the object.

19. The display switching method of claim 18, wherein, at the specifying step, the specified timing is set based on the echo signal itself.

20. The display switching method of claim 19, wherein, at the processing step, the three-dimensional image data are projected to the two-dimensional image data using a specified projection technique serving as the specified processing technique and, at the switchover step, the projection technique is switched at the specified injection timing.

21. A diagnostic ultrasound apparatus comprising:
a probe configured to transmit and receive an ultrasound beam;
a transmitter configured to transmit the ultrasound beam to scan a specified three-dimensional region of an object;
a receiver configured to receive an echo signal, emanated from the object in response to the transmission of the ultrasound beam;
a production unit configured to produce three-dimensional image data based on the echo signal and to produce two-dimensional image data from the three-dimensional image data using a specified processing technique;
a display unit configured to display the two-dimensional image data;
a detector configured to specify a timing when an ultrasound contrast agent that has been injected into the object begins to arrive at the three-dimensional region; and
a switchover unit configured to switch the processing technique at the specified injection timing.

22. The diagnostic ultrasound apparatus of claim 21, wherein the specifying unit is configured to automatically specify the timing after the ultrasound contrast agent has been injected into the object.

23. The diagnostic ultrasound apparatus of claim 22, wherein the specifying unit is configured to automatically specify the timing responsively to a signal given by a contrast agent injection apparatus used to inject the contrast agent.

24. The diagnostic ultrasound apparatus of claim 22, wherein the specifying unit is configured to set the specified timing based on the echo signal itself.

25. The diagnostic ultrasound apparatus of claim 24, wherein the specifying unit has at least one of a first comparing element for specifying the specified timing by making a comparison in strength between the echo signal emanated from a tissue of the object and the echo signal emanated from a blood flow thereof and a second comparing element for specifying the specified timing by making a comparison in strength between echo signals emanated from a blood flow of the object at two sequential timings.

26. The diagnostic ultrasound apparatus of claim 25, wherein the first and second comparing elements are configured to perform the comparison using either a sum and an average of intensity of at least part of the echo signal providing three-dimensional image data.

27. The diagnostic ultrasound apparatus of claim 25, wherein the first and second comparing elements are configured to perform the comparison using either a sum and an average of signal intensities of a group of signals constituting at least part of signals made up of the echo signal acquired at every spatial position in the three-dimensional region.

28. The diagnostic ultrasound apparatus of claim 25, wherein the first and second comparing elements are configured to perform the comparison using either a sum and an average over a certain period of time with respect to signal intensities of a group of signals constituting at least part of signals made up of the echo signal acquired at every spatial position in the three-dimensional region.

29. The diagnostic ultrasound apparatus of claim 21, wherein the processing unit is configured to project the three-dimensional image data to the two-dimensional image data using a specified projection technique serving as the specified processing technique and the switchover unit is configured to switch the projection technique at the specified injection timing.

30. The diagnostic ultrasound apparatus of claim 21, wherein the switchover unit is configured to switch a first display technique used as the processing technique before the ultrasound contrast agent arrives at the three-dimensional region to a second display technique used as the processing technique after the ultrasound contrast agent begins to arrive at the three-dimensional region.

31. The diagnostic ultrasound apparatus at claim 30, wherein the first display technique is configured to project the three-dimensional image data using a minimum intensity projection technique so that projected image data serving as the two-dimensional image data are produced and to display the projected image data.

32. The diagnostic ultrasound apparatus of claim 30, wherein the first display technique is configured to project the three-dimensional image data using a minimum intensity projection technique so that projected image data serving as the two-dimensional image data are produced, to reverse the projected image data in luminance gradations so that reversed projected image data are produced, and to display the reversed projected image data.

33. The diagnostic ultrasound apparatus of claim 30, wherein the first display technique is configured to reverse the produced three-dimensional image data in luminance gradations so that reversed three-dimensional image data are produced, to project the reversed three-dimensional image data using a maximum intensity projection technique so that projected image data serving as the two-dimensional image data are produced, and to display the projected image data.

34. The diagnostic ultrasound apparatus of claim 30, wherein the second display technique is configured to project the three-dimensional image data using a maximum intensity projection technique so that projected image data serving as the two-dimensional image data are produced and to display the projected data obtained.

* * * * *